United States Patent [19]

Stahly

[11] 4,423,072

[45] * Dec. 27, 1983

[54] METHOD FOR IMPROVING THE METABOLIC STABILITY AND SURVIVAL OF NEONATAL PIGS

[75] Inventor: Tim S. Stahly, Lexington, Ky.

[73] Assignee: The University of Kentucky Research Foundation, Lexington, Ky.

[ * ] Notice: The portion of the term of this patent subsequent to May 11, 1999, has been disclaimed.

[21] Appl. No.: 368,007

[22] Filed: Apr. 13, 1982

Related U.S. Application Data

[63] Continuation-in-part of Ser. No. 107,886, Dec. 28, 1979, Pat. No. 4,329,359.

[51] Int. Cl.$^3$ .................... A61K 31/23; A61K 31/045
[52] U.S. Cl. .................................. 424/312; 424/313; 424/314; 424/343
[58] Field of Search ................ 424/343, 312, 313, 314

[56] References Cited

PUBLICATIONS

Seerley–Chem. Abst., vol. 93, (1980), p. 24,951g.

*Primary Examiner*—Sam Rosen
*Attorney, Agent, or Firm*—Birch, Stewart, Kolasch & Birch

[57] ABSTRACT

A method of improving the metabolic stability of neonatal pigs and increasing their survival rate by administering to the pregnant sow during its latter stages of gestation up to about 80 days prior to parturition an effective amount of a material selected from the group consisting of a dihydroxy alkanol having 3 to 10 carbon atoms; a triglyceride of glycerol and fatty acids wherein at least one of the fatty acid moieties containing 8 to 12 carbon atoms with the remaining acid moieties containing 13 to 20 carbon atoms; the mono and diol esters of said alkanols and said fatty acids wherein at least one of the fatty acid moieties contains 8 to 12 carbon atoms with the remaining acid moieties containing 13 to 20 carbon atoms; and the ester of said dihydroxy alkanol and fatty acids containing 13 to 20 carbon atoms.

8 Claims, No Drawings

METHOD FOR IMPROVING THE METABOLIC STABILITY AND SURVIVAL OF NEONATAL PIGS

BACKGROUND AND SUMMARY OF THE INVENTION

The present invention is a continuation-in-part of U.S. Ser. No. 107,886 filed Dec. 28, 1979, now U.S. Pat. No. 4,329,359 which issued May 11, 1982.

The present invention relates to an improved method for increasing the survival rate of baby pigs. More particularly, the present invention is directed to a method of increasing the survival rate of baby pigs by using a food supplement in the diet of a pregnant pig.

The low survival rate observed in baby pigs, e.g., 20 to 30% mortality between birth and weaning, is attributed largely to two factors:

(1) the high degree of metabolic immaturity in the newborn pig and (2) an insufficient energy intake by the pig in its first 2 or 3 days of life. The magnitude of this loss can be emphasized by the fact that each 1% improvement in pig survival will generate an additional $2.00 to $6.00 profit per litter.

The major metabolic defects observed in the newborn pig are summarized as follows:

1. A low level of phosphorylase potentially decreases the rate of production of glucose from glycogen stores;
2. A defective gluconeogenic capacity limits the supply of glucose available to animals exposed to nutritional and/or environmental stress;
3. A deficient hepatic mitochondria number limits the use of carbohydrates as well as fatty acids for energy production;
4. A small amount of body fat impairs both thermoinsulation and the quantitative contribution of fat as a major energy source; and
5. A low level of amino acid degradating enzymes tends to limit the availability of amino acids as a substrate source (carbon skeletons) for gluconeogenesis.

More specifically, the high mortality rate observed in pigs is attributed largely to the newborn pigs impaired thermostability and defective gluconeogenic capacity and its inability to obtain a sufficient energy intake from the sow's milk during its first 2 or 3 days of life. Because of these major metabolic defects, as well as the others set forth hereinabove, particularly its low gluconeogenic capacity, the neonatal pig rapidly develops hypoglycemia after birth if not permitted to suckle or if subject to cold stress.

This rapid onset of hypoglycemia in the newborn pig is the result of 95% of the pig's energy reserves in the form of glycogen being used within the first 72 hours of birth regardless of whether the pig is suckled or not by the sow. The significance of the baby pig's susceptibility to hypoglycemia is indicated by the 30 to 50% death loss observed within 72 hours after birth when baby pigs are fasted from birth or when baby pigs are fed for 6 hours after birth and then fasted.

Research has been conducted to identify factors which would reduce baby pig mortality. These investigations have suggested that the existence of physiological conditions, i.e., diabetes, starvation, high dietary fat intake, etc., which are associated with elevated blood ketone levels in the sow, may result in heavier, more metabolically stable pigs at birth.

Accordingly, an object of the present invention is to provide an improved method for increasing the survival rate of baby pigs.

A further object of the present invention is to provide a method for improving the metabolic stability of the newborn pig by preventing the development of hypoglycemia in the neonatal pig shortly after birth.

Still another object of the present invention is to provide a food supplement which is effective in elevating the ketone levels in blood of the pregnant pig.

A still further object of the present invention is to provide a food supplement which is effective in elevating the ketone levels in blood of the pregnant pig.

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Pursuant to the present invention, it has been determined that the administration of specific alcohols, esters and glycerides to female pigs during late stages of gestation effectively increases the liver glycogen stores in the pig at birth and prolongs the availability of the liver glycogen stores in the newborn pig. This increased availability of glycogen delays the onset of hypoglycemia in the pig and increases the survival rate (percent of pigs born alive that survive to weaning) of neonatal pigs.

The alcohols, esters and glycerides which can be effectively used in accordance with the present invention fall into the following categories:

1. Dihydroxy alkanols having 3 to 20 carbon atoms, such as for example 1,3-Butanediol.

2. The mono- and diesters of the dihydroxy alkanols having 3 to 10 carbon atoms and fatty acids having 8 to 20 carbon atoms wherein at least one of the fatty acid moieties contains 8 to 12 carbon atoms (medium chain length) with the remaining acid moiety, if any, containing 13 to 20 carbon atoms (long chain length). Exemplary of such esters is 1,3-Butanediol monooctanoate.

3. A triglyceride of glycerol and fatty acids having 8 to 20 carbon atoms wherein at least one of the fatty acid moieties contains 8 to 12 carbon atoms, with the remaining acid moiety, if any, containing 13 to 20 carbon atoms.

4. The mono- and diesters of dihydroxy alkanols having 3 to 10 carbon atoms and fatty acids containing 13 to 20 carbon atoms.

When considering the dihydroxy alkanols or esters thereof as a suitable additive, the hydroxy constituent must be on the first and third carbon atom to minimize any possible toxic effect. If the alkanols contain three or more OH groups, the additional OH groups above two are advantageously positioned on the odd carbon atoms. Also, in categories 2 and 3 above it is important that at least some medium chain fatty acid be present in the moiety. For example, the following differences in intestinal absorption and metabolism of medium chain triglycerides (MCT) and long chain triglyerides (LCT) are known to exist in mammals.

1. MCT are absorbed and metabolized more rapidly than LCT.

2. The intestinal absorption of MCT does not require the presence of bile salts or pancreatic lipase; whereas, the absorption of LCT is entirely dependent on whether or not a sufficient quantity of bile salts and pancreatic lipase are present to emulsify and hydrolize the LCT. MCT may be absorbed intact and still be utilized by the animal because MCT may be completely hydrolyzed in the intestinal mucosal cell, whereas LCT cannot.

3. The intestine has a greater capacity to absorb MCT compared with LCT.

4. Fatty acids derived from MCT are transported to the liver for metabolism principally by the portal vein and not by the intestinal lymphatic system as are fatty acids from LCT.

5. Fatty acids derived from MCT are transported in a non-esterfied form; whereas fatty acids from LCT are re-esterfied following absorption and then form chylomicrons.

6. Medium chain fatty acids are more rapidly oxidized than those of long chain fatty acids by many tissues, including the liver, small intestine and the striated muscle.

7. In the liver, medium chain fatty acids are principally metabolized to $CO_2$, acetate and ketones. In contrast, long chain fatty acids are principally metabolized to triglycerides with only a small portion of the fatty acids being converted to $CO_2$ and ketones. Because of the preferential metabolism of medium chain fatty acids to $CO_2$ and ketones, MCT are poorly utilized for tissue lipid synthesis; whereas, LCT are directly deposited as lipid in tissue.

The rapid absorption and transportation of medium chain fatty acids to the liver and their preferential conversion to ketones rather than triglycerides in tissue represent unique metabolic characteristics of MCT compared with LCT. In other words, although both MCT and LCT are triglycerides of glycerol, MCT elicit a nutritional and physiological response in mammals unique from those of LCT.

For the above reasons the presence of medium chain fatty acids in categories 2 and 3 are essential. However, once having established the necessity of the presence of medium chain fatty acids, there are also some additional advantages to be gained by the presence of some long chain fatty acids together with the medium chain fatty acids. Thus the presence of some long chain fatty acids provides the additional benefits of an increase in the milk fat content, a tendency to increase body fat content of the pigs at birth and a tendency to increase the total amount of colostrum produced by the sow. With respect to category 4 above, since the dihydroxy alkanol portion of the ester provides the desired food supplement advantages, a long chain fatty alone can be used in forming the ester. However, the presence of the long chain fatty acids together with the alkanol in forming the ester does enhance the antimicrobial activity and thus may increase the pig survival rate when compared to the use of the dihydroxy alkanol alone.

The alkanols and the glycerides are administered to the pregnant pig as a food supplement, for example, as an addition to a corn-soybean meal diet. The alkanol supplement, for example, 1,3-Butanediol, which is a ketone former, has been found to be palatable and efficiently utilized by the pig when included as a food supplement to provide about 2 to 20% of the dietary energy in the pigs diet as shown in the following table. If the food supplement is administered over longer periods of time, i.e., up to about 80 days prior to parturition, then a smaller percentage of the dietary energy in the pig's diet, for example about 2 to 10% or more preferably 4 to 8%, can be effectively provided.

TABLE 1

1,3-Butanediol Supplementation in Growing Swine

| Trait | 1,3-Butanediol, % of dietary energy | | | | | |
|---|---|---|---|---|---|---|
|  | 0 | 8 | 17 | 25 | 33 | 42 |
| Wt. gain, kg | 19.5 | 20.5 | 21.4 | 11.9 | 4.3 | 1.1 |
| ME intake, Mcal | 197 | 212 | 219 | 157 | 85 | 77 |
| ME/wt gain, Mcal/kg | 10.1 | 10.3 | 10.2 | 13.2 | 19.8 | 70.0 |
| Plasma |  |  |  |  |  |  |
| B—hydroxybutyrate, nmole/ml | 159 | 415 | 457 | 425 | 831 | 980 |
| Acetoacetate, nmole/ml | 69 | 100 | 115 | 183 | 150 | 198 |
| Glucose, mg/dl | 75 | 72 | 95 | 97 | 142 | 119 |

B. R. Romsos, P. S. Belo, E. R. Miller & G. A. Leveille, 1975 Journal of Nutrition, Vol. 105, Page 16.

As can be seen from the table, higher dietary levels of 1,3-Butanediol, e.g., greater than 25% of the dietary energy, tend to depress feed consumption and subsequent growth.

Because ketones have shown to be readily transferred across the placenta, 1,3-Butanediol, a ketone former, represents a potential 'supplemental' energy source for the developing fetus. 1,3-Butanediol and its mono- and diesters have been shown to possess antimicrobial activity. Inclusion of antimicrobial agents in diets of pigs during late gestation and early lactation tends to increase the survival rate of neonatal pigs.

According to the present invention, it has been determined that a long-term administration of 1,3-Butanediol in sows during the latter stages of gestation results in an increased liver glycogen content in the newborn pig and an improved pig survival from birth to weaning. Advantageously, the administration of the specific food additive of the present invention can begin about 12 to 80 days, advantageously about 20 to 40 days prior to parturition and continue until parturition, during which about 2 to 20%, advantageously 4 to 8% of the dietary energy of the pig's diet is provided. After parturition, the sows are allowed to consume a standard lactation diet.

The following example is provided as being exemplary of the present invention and should not be considered as being limitative of the present invention.

EXAMPLE 1

Sixty-eight sows were fed isocaloric intakes (6800 kcal of metabolizable energy/sow/day) of a fortified corn-soybean meal diet plus an additional 1700 kcal of metabolizable energy in the form of starch or 1,3-Butanediol beginning approximately 8 days before parturition. After parturition, all sows were allowed to consume a standard lactation diet ad libitum. The results are shown in the following table:

TABLE 2

1,3-Butanediol Supplementation in Sows During Late Gestation.[a]

| Trait | Prepartum Treatment[a] | | Change |
|---|---|---|---|
|  | Control | 1,3-Butanediol |  |
| Pigs/litter |  |  |  |
| At birth | 10.39 | 10.14 |  |
| At weaning | 8.79 | 9.28 | +.49 |
| Avg. Pig Wt. (kg) |  |  |  |
| At birth | 1.20 | 1.26 | +.06 |
| At weaning | 3.51 | 3.58 | +.08 |

TABLE 2-continued

| 1,3-Butanediol Supplementation in Sows During Late Gestation.[a] | | | |
|---|---|---|---|
| | Prepartum Treatment[a] | | |
| Trait | Control | 1,3-Butanediol | Change |
| Pig Survival, % | 85.30 | 92.00 | +6.7 |

[a]Thirty-eight and 40 litters represented in the control and 1,3-Butanediol treatments, respectively.

As can be seen from the above table, the 1,3-Butanediol supplementation did not influence the number of live pigs born/litter (10.14 vs. 10.39) or the average pig weights (g) at birth (1,259 vs 1,205) or at weaning (3575 vs 3510) compared to those of litters from sows fed starch. However, 1,3-Butanediol supplementation did increase the total number of pigs weaned/litter (9.28 vs 8.79) and the percent of pigs born alive (92.0 vs 85.3) that survived to weaning compared to those of the starch treatment group. Sow feed intake and weight gain during lactation were not affected by dietary treatment.

In a second experiment, the addition of 1,3-Butanediol to the diet of sows during late gestation was shown to increase the metabolic stability of the newborn pig by increasing the level of liver glycogen present in the pig at birth and delaying the onset of hypoglycemia in pigs which were allowed to nurse or were fasted from birth to 12 hr of age (Table 3). In addition, the colostrum of sows fed 1,3-Butanediol contained a higher percent fat than that of sows fed the control diet (Table 4).

TABLE 3

| Effect on 1,3-Butanediol Supplementation in Sows During Late Gestation on Plasma Glucose and Liver Glycogen Stores in Neonatal Pigs.[a] | | | |
|---|---|---|---|
| Age of Pig, hr | Feeding Regime | Prepartum Treatment[a] | |
| | | Control | 1,3-Butanediol |
| | | Liver glycogen, g | |
| 0 | — | 3.47 | 4.30 |
| 12 | Nursed | .70 | .85 |
| 12 | Fasted | .48 | .96 |
| | | Blood glucose, mg/dl | |
| 0 | — | 137.6 | 128.7 |
| 12 | Nursed | 92.7 | 124.2 |
| 12 | Fasted | 84.7 | 93.8 |

[a]Thirty and 42 pigs represented in the control and 1,3-Butanediol treatments, respectively.

TABLE 4

| Effect of 1,3-Butanediol Supplementation in Sows During Late Gestation on the Fat and Protein Content of Sow's Colostrum.[a] | | |
|---|---|---|
| | Prepartum Treatment[a] | |
| Hr Postpartum | Control | 1,3-Butanediol |
| | Colostrum fat, % | |
| 0 | 2.7 | 4.3 |
| 12 | 3.1 | 3.9 |
| | Colostrum protein, % | |
| 0 | 13.8 | 15.1 |
| 12 | 10.5 | 10.5 |

[a]Ten and fourteen samples represented in the control and 1,3-Butanediol treatments, respectively.

EXAMPLE 2

A varying number of sows as noted in Tables 5 and 6 below were fed a fortified corn-soybean meal diet containing as a food supplement an additional amount of metabolizable energy in the form of 1,3-Butanediol representing about 20% of the dietary energy in the sow's diet. The sows were fed the butanediol for periods varying from 4 to 20 days prior to parturition and continuing until parturition. A number of similar runs were made in which the sows' diet was not supplemented with 1,3-Butanediol. The percentage survival of the baby pigs where the diet of the sow was supplemented with 1,3-Butanediol was compared with that where no 1,3-Butanediol was administered. The results are shown in the following tables wherein the results recorded therein represent data recorded at 14 days after birth in Table 5 and 28 days after birth in Table 6. The average improvement in pig survival for Tables 5 and 6 is 6.38% and 10.8%, respectively.

TABLE 5

| Days Administered prior to Parturition | 4 | 5 | 6 | 7 | 8 | 9 | 10 | 11 |
|---|---|---|---|---|---|---|---|---|
| No. of Sows Observed | 13 | 13 | 17 | 19 | 16 | 10 | 8 | 9 |
| % Survival of Baby Pigs w/o 1,3-Butanediol | 75.0 | 85.9 | 78.4 | 86.2 | 80.2 | 91.9 | 79.9 | 71.9 |
| No. of Sows Observed | 18 | 13 | 19 | 18 | 14 | 10 | 10 | 4 |
| % Survival of Baby pigs with 1,3-Butanediol | 85.2 | 92.0 | 89.4 | 85.1 | 81.5 | 87.6 | 90.0 | 88.5 |
| % Gain or Loss | +10.2 | +6.1 | +11.0 | −1.1 | +1.3 | −4.3 | +10.1 | +16.6 |
| Days Administered prior to Parturition | 12* | 13 | 14 | 15 | 16 | 17 | 18* | 19* | 20* |
| No. of Sows Observed | 1 | 5 | 3 | 5 | 3 | 5 | 1 | 2 | 1 |
| % Survival of Baby Pigs w/o 1,3-Butanediol | 87.5 | 56.3 | 73.8 | 83.8 | 92.9 | 80.4 | 87.5 | 77.5 | 90.9 |
| No. of Sows Observed | 1 | 4 | 4 | 4 | 3 | — | 1 | 2 | 2 |
| % Survival of Baby Pigs with | 50.0 | 79.7 | 88.8 | 85.4 | 84.6 | — | 16.7 | 84.4 | 95.0 |

TABLE 5-continued

| 1,3-Butanediol % Gain or Loss | — | +23.4 | +15.0 | +1.6 | −8.3 | — | — | — | — |

Discounting the one and two sow observations (as noted by the *) as not being representative data and other observations where no data was recovered, the average improvement in percentage of pigs which survived was 6.38%.

TABLE 6

| Days Administered prior to Parturition | 4 | 5 | 6 | 7 | 8 | 9 | 10 | 11 |
|---|---|---|---|---|---|---|---|---|
| No. of Sows Observed | 12 | 11 | 16 | 16 | 16 | 7 | 6 | 7 |
| % Survival of Baby Pigs w/o 1,3-Butanediol | 73.6 | 84.2 | 78.0 | 90.0 | 77.1 | 87.3 | 80.0 | 64.2 |
| No. of Sows Observed | 15 | 11 | 17 | 12 | 11 | 9 | 8 | 2 |
| % Survival of Baby Pigs with 1,3-Butanediol | 80.2 | 91.8 | 85.6 | 88.2 | 78.7 | 83.7 | 92.8 | 100.0 |
| % Gain or Loss | +6.6 | +7.6 | +7.6 | −1.8 | +1.6 | −3.6 | +12.8 | |

| Days Administered prior to Parturition | 12* | 13 | 14 | 15 | 16* | 17 | 18* | 19* | 20* |
|---|---|---|---|---|---|---|---|---|---|
| No. of Sows Observed | 1 | 4 | 3 | 5 | 2 | 3 | 1 | 2 | 1 |
| % Survival of Baby Pigs w/o 1,3-Butanediol | 87.5 | 55.3 | 59.5 | 80.8 | 89.3 | 73.1 | 87.5 | 77.5 | 90.9 |
| No. of Sows Observed | — | 4 | 4 | 4 | 3 | — | 1 | 2 | 2 |
| % Survival of Baby Pigs with 1,3-Butanediol | — | 76.9 | 88.8 | 85.5 | 84.5 | — | 16.6 | 84.4 | 95.0 |
| % Gain or Loss | — | +21.6 | +29.3 | +4.7 | −4.8 | — | — | — | — |

Discounting the one and two sow observations (as noted by the *) as not being representative data and other observations where no data was recovered, the average improvement in percentage of pigs which survived was 10.8%.

What is claimed is:

1. A method of improving the metabolic stability of neonatal pigs and increasing their survival rate which comprises administering to a pregnant sow during its latter stages of gestation, up to about 80 days prior to parturition, an effective amount of a material selected from the group consisting of
   (1) a dihydroxy alkanol having 3 to 10 carbon atoms;
   (2) a triglyceride of glycerol and fatty acids wherein at least one of the fatty acid moieties contains 8 to 12 carbon atoms with the remaining acid moieties containing 13 to 20 carbon atoms;
   (3) the mono and diol esters of said dihydroxy and said fatty acids wherein at least one of the fatty acid moieties contains 8 to 12 carbon atoms with the remaining acid moieties containing 13 to 20 carbon atoms; and
   (4) the ester of said dihydroxy alkanol and said fatty acids containing 13 to 20 carbon atoms.

2. The method of claim 1 wherein the dihydroxy alkanol is 1,3-Butanediol.

3. The method of claim 1 wherein the alkanol, the triglyceride or the mono and diol ester of said alkanols and fatty acids are added as a food supplement to the sow's diet.

4. The method of claim 3 wherein the alkanol, the triglyceride or the mono and diol ester of said alkanols and fatty acids are added in an amount sufficient to provide about 2 to 20% of the dietary energy in the sow's diet.

5. The method of claim 1 wherein the alkanol, the triglyceride and the mono and diol esters of said alkanols and fatty acids are administered about 12 to 40 days before parturition and continued until parturition.

6. The method of claim 1 wherein the monoester is 1,3-Butanediol monooctanoate.

7. The method of claim 1 wherein the alkanol, the triglyceride or the mono and diol ester of said alkanols and fatty acids are added in an amount sufficient to provide about 4 to 8% by the dietary energy in the sow's diet.

8. The method of claim 1 wherein the OH groups of the dihydroxy alkanol are on the first and third carbon atoms.

* * * * *